United States Patent [19]

Atlani et al.

[11] Patent Number: 4,504,287
[45] Date of Patent: Mar. 12, 1985

[54] METHOD OF PURIFYING A GAS MIXTURE CONTAINING UNDESIRABLE GAS COMPOUNDS

[75] Inventors: Martial Atlani, Paris; Roben Loutaty, Le Havre; Claude Wakselman, Villebon sur Yvette; Charles Yacono, Le Havre, all of France

[73] Assignees: Compagnie Francaise de Raffinage; Agence Nationale de Valorisation de la Recherche (ANVAR), both of France

[21] Appl. No.: 417,211

[22] Filed: Sep. 13, 1982

[30] Foreign Application Priority Data

Sep. 11, 1981 [FR] France .................. 81 17233

[51] Int. Cl.³ .................................... B01D 19/00
[52] U.S. Cl. .................................... 55/53; 55/68; 55/73; 423/226
[58] Field of Search .................. 55/68, 73, 40, 44, 53; 423/226

[56] References Cited

U.S. PATENT DOCUMENTS

| | | | |
|---|---|---|---|
| 2,781,863 | 2/1957 | Bloch et al. | 55/53 |
| 3,632,519 | 1/1972 | Gustafson | 55/68 |
| 3,880,615 | 4/1975 | Grunewald | 55/44 |
| 4,251,493 | 2/1981 | Randell | 423/226 |
| 4,336,233 | 6/1982 | Appl et al. | 55/68 |

FOREIGN PATENT DOCUMENTS 2315001 10/1974 Fed. Rep. of Germany .......... 55/73

Primary Examiner—Bernard Nozick
Attorney, Agent, or Firm—Scully, Scott, Murphy & Presser

[57] ABSTRACT

The invention relates to a method for purifying a gas mixture containing at least one undesirable gas compound utilizing certain sulfonamide or sulfamide solvents.

6 Claims, 1 Drawing Figure

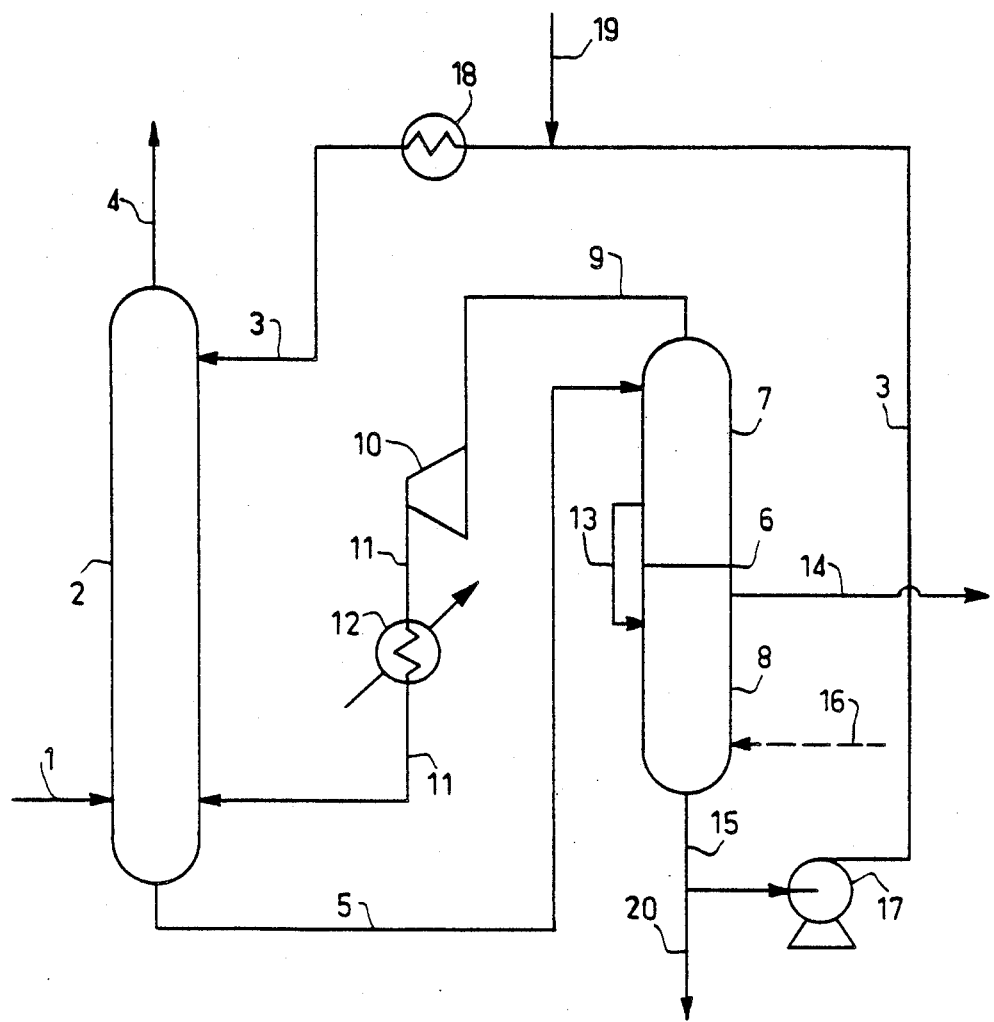

METHOD OF PURIFYING A GAS MIXTURE CONTAINING UNDESIRABLE GAS COMPOUNDS

BACKGROUND OF THE INVENTION

The present invention relates to a method of purifying a gas mixture containing undesirable gas compounds and more particularly to the elimination of undesirable compounds such as oxides of carbon, particularly carbon dioxide, the hydrogen and carbonyl sulfides and the alkylthiols.

In accordance with the present invention, the term gaseous mixture to be purified means a natural gas mixture such as natural gas, or a mixture of gases obtained in the course of chemical reactions, particularly in the refining industry. This gas mixture can contain, in particular, aside from at least one of the undesirable gas compounds cited above, hydrocarbons, and/or hydrogen.

Present methods of purifying gas mixtures generally involve one of the three operations below:
absorption by a liquid
absorption by a solid
chemical conversion, essentially in the presence of a catalyst.

The first operation, which is often preferred, for the elimination from gas mixtures of undesirable compounds such as those defined above, involves two types of solvent, separately or in conjunction:

"chemical" solvents that extract the undesirable compounds by a chemical reaction, and restore them following a heating perhaps accompanied by a decompression, "physical" solvents that absorb the gases under pressure by dissolution in a liquid, and desorbing them by decompression.

The physical solvents prove to be particularly interesting for gas mixtures brought under high pressure and containing a large percentage of undesirable compounds. Under these conditions, the "physical" solvents have greater absorption capacity than the "chemical" solvents. This advantage results in a lower proportion of solvent to be used, a reduction in the size of the equipment, and in the cost of utilities.

SUMMARY OF THE INVENTION

It is therefore an object of the present invention to propose solvents particularly adapted to the absorption of the undesirable compounds contained in gas mixtures.

Accordingly, these and other objects are accomplished herein by a method of purifying a gas mixture containing at least one undesirable gas compound, said method comprising:
(a) a first stage of absorption with the aid of a solvent of the undesirable gas compounds, said first stage leading:
on the one hand to a gas mixture that is at least partially purified,
on the other hand, to a solution of the undesirable compounds in the solvent,
(b) a second stage of desorption of the undesirable compounds from the solution, said second stage leading:
on the one hand to the obtention of at least one undesirable gas compound,
on the other hand, to the obtention of solvent which can be recycled to the first stage,
said method being characterized in that the solvent is comprised at least in part by at least one compound which contains, in its molecular structure, at least one group:

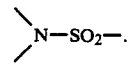

BRIEF DESCRIPTION OF THE DRAWINGS

The sole figure is a simplified diagram of an industrial unit for carrying out the process of the present invention.

DETAILED DESCRIPTION OF THE INVENTION

The compounds that can br used in the method according to this invention comprise, in particular, sulfonamides and sulfamides.

The sulfonamides that can be used in the method according to this invention, can be selected, in particular, from the group consisting of:
(1) the compounds of the general formula:

in which R', R" and R''' can be saturated or unsaturated alkyl or aryl radicals.

In the case of alkyl radicals, the latter can be linear or branched, and can have 1 to 18 carbon atoms. Moreover, at least one of the radicals R" and R''' can be replaced by a hydrogen atom.

(2) The compounds of the general formula:

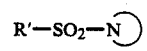

in which R' is a radical such as the radical R' in formula (1) and in which the nitrogen atom is part of a cyclic group comprised of, aside from the nitrogen, 2 to 5 carbon atoms, and able to contain, aside from the nitrogen, a heteroatom such as oxygen, for example; and
(3) the compounds of the general formula:

in which R' is a radical, such as the radical R' in formulas (1) and (2), and in which the group

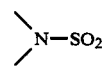

belongs to a cyclic structure comprised of, aside from the said group, 2 to 4 carbon atoms, and able to contain a heteroatom such as oxygen, for example.

Among the compounds (1) defined above, it is possible to cite, for example:
— N-methylmethane sulfonamide
— N-methylethane sulfonamide
— N-ethylmethane sulfonamide
— N-ethylethane sulfonamide
— N-propylmethane sulfonamide
— N-isopropylmethane sulfonamide
— N,N-diethylmethane sulfonamide
— N,N-dimethylmethane sulfonamide
— N,N-dimethylethane sulfonamide
— N,N-diethylethane sulfonamide
— N,N-diallylmethane sulfonamide
— N,N-methylallylmethane sulfonamide.

Among the compounds (2) defined above, it is possible to cite for example:
— N-ethanesulfonylpyrrolidine
— N-ethanesulfonylpiperidine
— N-ethanesulfonylmorpholine Among the compounds (3) defined above, it is possible to cite, for example:
— N-methylpropane sultam
— N-ethylpropane sultam
— N-butylpropane sultam.

The sulfamides that can be used in the method according to the invention herein can be selected, in particular, from the sulfamides of the general formula:

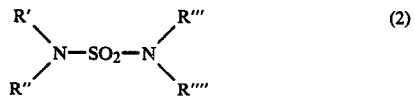

in which R', R'', R''' and R'''' are saturated, linear or branched, identical or different alkyl radicals, having 1 to 4 carbon atoms.

It is possible to cite, for example, tetra ethyl sulfamide.

The operational conditions of the first stage of absorption of the undesirable compounds depend on the nature of the gas mixture to be purified, and on the nature of the sulfonamide.

By way of example, for a gas mixture containing at least one light hydrocarbon such as methane, ethane or propane, and undesirable compounds such as hydrogen sulfide and carbon dioxide, the operational conditions can be as follows:
temperature comprised between 5° and 100° C.,
pressure comprised between 4 and 400 bars,
proportion of solvent, that is to say the ratio:

$$\frac{\text{molar flow of solvent}}{\text{molar flow of gas mixture to be purified}}$$

comprised between 0.05 and 15.

The stage of desorption of the undesirable compounds can be conducted in one or more operations, by decompression and, perhaps heating of the solution obtained in the course of the first stage, with, perhaps, an entrainment by a gas such as nitrogen.

The sole figure of the drawing in the present description represents, by way of non-limiting example, a simplified diagram of an industrial unit for implementation of the method according to the invention.

According to this diagram, line 1 introduces, into the bottom of an absorption column 2 working in reflux, a gas mixture to be purified, and containing methane, ethane, propane and undesirable gases which are to be eliminated, namely, hydrogen sulfide and carbon dioxide.

It is understood that this does not constitute a limiting example, and that this gas can contain other undesirable compounds such as carbonyl sulfide or alkylthiols.

Column 2 can be, for example, a packed column or a plate column. This column can work at a temperature which can be comprised between 5° and 100° C. and a pressure which can be comprised between 4 and 400 bars.

The proportion of solvent introduced through line 3, into the top of column 2, which is the ratio, as indicated above:

$$\frac{\text{molar flow of solvent}}{\text{molar flow of gas mixture to be purified}}$$

can be comprised between 0.05 and 15.

At the top of column 2, the gas to be purified is collected through line 4, freed of the greater part of the hydrogen sulfide and carbon dioxide in it. The dimensions of the column and the operational conditions thereof are selected as a function of the flow and the purity of the gas collected by line 4, which it is desired to obtain.

At the bottom of column 2, a solution of hydrogen sulfide and carbon dioxide in the solvent is collected by line 5. This solution also contains a small quantity of the hydrocarbons found in the gas to be purified, and introduced through line 1.

It is then necessary to regenerate the solvent, that is to say, in the present case, to extract the hydrogen sulfide and carbon dioxide therefrom.

Various schemes can be envisaged. This figure represents a regeneration in two stages.

The solution collected by line 5 is led into a unit constituted by two stages 7 and 8. The solution is first introduced into stage 7, where the pressure is maintained at a pressure below that in column 2, but higher than 1 bar. At the top of stage 7, through line 9, a mixture of hydrocarbons, and perhaps a little hydrogen sulfide and carbon dioxide are collected.

This mixture, after recompression in a compressor 10, is recycled to column 2 through line 11, after passage through a cooler 12 designed to reduce the temperature of the mixture, which was heated as a result of the recompression, to the working temperature of column 2.

The solution containing the greater part of hydrogen sulfide and carbon dioxide, is collected by line 13 at the bottom of stage 7, and is conducted into stage 8. The pressure inside stage 8 is lower than that of stage 7 and equal to or higher than 1 bar.

At the top of stage 8, the hydrogen sulfide and carbon dioxide are collected through line 14. At the bottom of stage 8, the solvent freed of hydrogen sulfide and carbon dioxide is collected through line 15.

It is possible to equip stage 8 with a device for entrainment of the hydrogen sulfide and carbon dioxide by a gas. With this in mind it is possible to introduce, through line 16, into stage 8, nitrogen or air, which will be evacuated through line 14 at the same time as the hydrogen sulfide and carbon dioxide.

The regeneration of the solvent can be completed by a heating operation (not shown).

The solvent collected by line 15 is recycled, after passage in a pump 17, to line 3.

Line 3 can be equipped with an exchanger 18 which can be a cooler or a heater, designed to bring the solvent to the working temperature of column 2.

The installation can be equipped with a solvent make-up (line 19) and a solvent purge (line 20).

A water scrubbing of the gas effluents, not shown, can limit the possibilities of solvent loss.

The following examples are provided to illustrate the invention in non-limiting fashion.

The HENRY constant designated below by letter H, is the ratio:

$$H = \frac{\text{partial pressure of the gas}}{\text{molar fraction of the gas in solution in the solvent considered}}$$

It is expressed in units of pressure.

It is found that as H is higher, less gas is dissolved.

Table 1 below shows the HENRY constants for several gases considered and for several solvents.

The constants, expressed in atmospheres, are designated by the letter H plus the chemical formula of the gas considered.

TABLE 1

| SULFONAMIDE | HENRY CONSTANTS | | | | | | |
|---|---|---|---|---|---|---|---|
| | $H_{C_2H_6}$ | $H_{C_3H_8}$ | $H_{C_4H_{10}}$ | $H_{CO_2}$ | $H_{H_2S}$ | $H_{SHCH_3}$ | $H_{COS}$ |
| N,N—diethyl methane sulfonamide | 143.5 | 54.4 | 18.9 | 56.1 | 11.8 | 2.2 | 26.1 |
| N,N—dimethyl ethane sulfonamide | 182.0 | 69.1 | 25.7 | 63.3 | 12.3 | 3.1 | 32.8 |
| N—ethyl methane sulfonamide | 292.6 | 132.1 | 61.4 | 94.5 | 22.8 | 5.5 | 59.3 |
| N,N—methyl ethyl methane sulfonamide | 192.2 | 82.3 | 30.3 | 68.4 | 13.5 | 2.5 | 33.8 |
| N—ethyl propane sultame | 244.8 | 93.4 | 38.5 | 65.2 | 12.1 | 2.2 | 26.8 |
| N,N—diallyl methane sulfonamide | 111.5 | 41.0 | 14.5 | 49.2 | 11.8 | 2.0 | 20.1 |
| N—ethane sulfonyl pyrrolidine | 123.6 | 57.0 | 21.5 | 64.9 | 10.0 | Not Measured | |
| Tetraethylsulfamide | 54.5 | 21.8 | 7.3 | 41.2 | 8.9 | Not Measured | |

EXAMPLE 1

This example is intended to illustrate the efficiency of the extraction of various undesirable gases by the method according to the invention with the aid of various solvents.

The HENRY constants at infinite dilution at 25° C. are measured on ethane, propane, normal butane, carbon dioxide, hydrogen sulfide, methyl mercaptan and carbonyl sulfide.

These HENRY constants were determined using the technique described by D. RICHON and H. RENON in the article entitled "Infinite dilution HENRY'S constants of light hydrocarbons in N-hexadecane, N-octadecane and 2,2, 4,4,6,8,8,-hepta methyl nonane by inert gas stripping", in the Journal of Chemical Engineering Data, volume 25, No. 1, pages 59 and 60 (1980).

Table 2 below regroups certain ratios of HENRY constants taken two by two.

TABLE 2

| SULFON-AMIDE | RATIO OF HENRY CONSTANTS | | | | | | | | | |
|---|---|---|---|---|---|---|---|---|---|---|
| | $\frac{H_{C_2H_6}}{H_{CO_2}}$ | $\frac{H_{C_2H_6}}{H_{H_2S}}$ | $\frac{H_{C_3H_8}}{H_{H_2S}}$ | $\frac{H_{C_4H_{10}}}{H_{H_2S}}$ | $\frac{H_{CO_2}}{H_{H_2S}}$ | $\frac{H_{C_2H_6}}{H_{SHCH_3}}$ | $\frac{H_{C_3H_8}}{H_{SCH_4}}$ | $\frac{H_{C_4H_{10}}}{H_{SHCH_3}}$ | $\frac{H_{C_2H_6}}{H_{COS}}$ | $\frac{H_{C_3H_8}}{H_{COS}}$ |
| N,N—diethyl methane sulfonamide | 2.56 | 12.2 | 4.61 | 1.60 | 4.75 | 65.2 | 24.7 | 8.59 | 5.50 | 2.08 |
| N,N—dimethyl ethane sulfonamide | 2.87 | 14.8 | 5.62 | 2.09 | 5.15 | 58.7 | 22.3 | 8.29 | 5.55 | 2.11 |
| N—ethyl methane sulfonamide | 3.10 | 12.8 | 5.79 | 2.69 | 4.14 | 53.2 | 84.0 | 11.2 | 4.93 | 2.23 |
| N,N—methyl ethyl methane sulfonamide | 2.81 | 14.2 | 6.10 | 2.24 | 5.07 | 76.9 | 32.9 | 12.1 | 5.69 | 2.43 |
| N—methyl propane sultame | 3.75 | 20.2 | 7.72 | 3.18 | 5.39 | 111.3 | 42.5 | 17.5 | 9.13 | 3.48 |
| N,N—diallyl methane sulfonamide | 2.27 | 9.45 | 3.47 | 1.23 | 4.17 | 55.8 | 20.5 | 7.25 | 5.55 | 2.04 |
| N—ethane sulfonyl pyrrolidine | 1.90 | 12.4 | 5.70 | 2.15 | 6.49 | | | | | |
| Tetraethylsulfamide | 1.32 | 6.1 | 2.5 | 0.82 | 4.62 | | | | | |

The higher the ratio, the better the separation.

Table 2 shows the possibility of the following separations by the method according to the invention:
ethane—carbon dioxide
ethane—hydrogen sulfide,
propane—hydrogen sulfide,
normal butane—hydrogen sulfide,
carbon dioxide—hydrogen sulfide,
ethane—methyl thiol,
propane—methyl thiol,
normal butane—methyl thiol,
ethane—carbonyl sulfide,
propane—carbonyl sulfide.

The method according to the invention therefore permits an efficient separation of undesirable gases, such as carbon dioxide, hydrogen sulfide, methyl thiol and carbonyl sulfide, from cases containing them. It can serve for the selective absorption of hydrogen sulfide, in the event the gas mixture contains carbon dioxide and hydrogen sulfide simultaneously.

EXAMPLE 2

This example relates to the elimination of hydrogen sulfide and carbon dioxide from a gas mixture with the aid of N,N-dimethyl ethane sulfonamide.

The gas mixture, a natural gas, has the following molar composition:

| methane: | 73% |
| ethane: | 1.5% |
| propane: | 0.5% |
| hydrogen sulfide: | 15% |
| carbon dioxide: | 10% |

The gas mixture is introduced into the bottom of an absorption column having 10 theoretical stages, fed at the top with N,N-dimethyl ethane sulfonamide.

The temperature and pressure inside the column are, respectively, 25° C. and 100 bars. The solvent proportion is 0.4.

At the top of the column, the purified gas is collected, with a molar composition as follows:

| methane: | 93.1% |
| ethane: | 1.6% |
| propane: | 0.4% |
| hydrogen sulfide: | <2 p.p.m., |
| carbon dioxide | 4.9%, |

The solution collected at the bottom of the column has the following composition:

| methane: | 4.6%, |
| ethane: | 0.5%, |
| propane: | 0.3%, |
| hydrogen sulfide: | 23.1%, |
| carbon dioxide: | 9.7%, |
| N,N—dimethyl ethane sulfonamide: | 61.8%, |

This example clearly shows the effectiveness of the method according to the invention for eliminating hydrogen sulfide and carbon dioxide from natural gas.

Obviously, other modifications and variations of the present invention are possible in the light of the above teachings. It is, therefore, to be understood that changes may be made in the particular embodiments of this invention which are within the full intended scope of the invention as defined by the appended claims.

We claim:

1. A method for purifying a gas mixture of hydrocarbons and/or hydrogen, said gas mixture additionally containing at least one undesirable gas compound selected from the group consisting of carbon monoxide, carbon dioxide, hydrogen sulfide, carbonyl sulfide and alkylthiols, comprising:

(a) in a first stage, absorption of said undesirable gas compounds in a solvent; and (b) in a second stage, desorption of said undesirable gas compounds from solution, said solvent being characterized as containing at least one compound comprising a sulfonamide selected from the group consisting of:

(1) the compounds of the general formula:

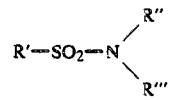

wherein R' is a saturated or unsaturated alkyl or aryl radical, R" and R'" are hydrogen, saturated or unsaturated alkyl or aryl radicals; the alkyl radicals are linear or branched and have 1 to 18 carbon atoms, —N-ethanesulfonylpyrrolidine,—N-ethanesulfonylpiperidine,—N-ethanesulfonylmorpholine, —N-methylpropane sultam,—N-ethylpropane sultam —N-butylpropane sultam and a sulfamide having the general formula:

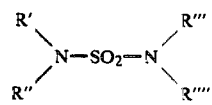

wherein R', R", R'" and R"" are linear or branched, saturated, the same or different, alkyl radicals, having 1 to 4 carbon atoms.

2. The method according to claim 1 wherein the sulfonamide of formula (1) is selected in the group consisiting of:

—N-methylmethane sulfonamide,
—N-methylethane sulfonamide,
—N-ethylmethane sulfonamide,
—N-ethylethane sulfonamide,
—N-propylmethane sulfonamide,
—N-isoproplymethane sulfonamide,
—N-diethylmethane sulfonamide,
—N-dimethylmethane sulfonamide,
—N,N-dimethylethane sulfonamide,
—N,N-diethylethane sulfonamide,
—N,N-diallylmethane sulfonamide,
—N,N-methylallylmethane sulfonamide.

3. The method according to claim 1, wherein the sulfanamide of formula (2) is tetraethyl sulfamide.

4. The method according to claim 1, wherein the absorption stage is conducted at a temperature in the range of from 5° to 100° C.

5. The method according to claim 1, wherein the absorption stage is conducted at a pressure in the range of from 4 to 400 bars.

6. The method according to claim 5 wherein the ratio of the molar flow of solvent to the molar flow of gas mixture to be purified is in the range of from 0.05 to 5.

* * * * *